US009622887B2

(12) United States Patent
Ducke et al.

(10) Patent No.: US 9,622,887 B2
(45) Date of Patent: Apr. 18, 2017

(54) STENT GRAFT WITH VALVE ARRANGEMENT

(71) Applicant: COOK MEDICAL TECHNOLOGIES LLC, Bloomington, IN (US)

(72) Inventors: Werner D. Ducke, Eight Mile Plains (AU); Chantelle King, Woodridge (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/530,866

(22) Filed: Nov. 3, 2014

(65) Prior Publication Data
US 2015/0127089 A1    May 7, 2015

(30) Foreign Application Priority Data

Nov. 4, 2013  (AU) .................. 2013254913

(51) Int. Cl.
A61F 2/07 (2013.01)
A61F 2/856 (2013.01)
(Continued)

(52) U.S. Cl.
CPC ............ *A61F 2/856* (2013.01); *A61F 2/07* (2013.01); *A61F 2/86* (2013.01);
(Continued)

(58) Field of Classification Search
CPC .... A61F 2/07; A61F 2/86; A61F 2/856; A61F 2002/061; A61F 2002/072;
(Continued)

(56) References Cited

U.S. PATENT DOCUMENTS 4,902,508 A    2/1990 Badylak et al.
5,711,969 A    1/1998 Patel et al.
(Continued)

FOREIGN PATENT DOCUMENTS

EP    2522306 A1    11/2012
EP    2609895 A2    7/2013
(Continued)

OTHER PUBLICATIONS

Tam Huynh, Ginger Abrham, James Murray, Kelvin Brockbank, Per-Otto Hagen, and Susan Sullivan, Remodeling of an Acellular Collagen Graft into a Physiologically Responsive Neovessel, Nature Biotechnology, vol. 17, Nov. 1999, pp. 1083-1086.
(Continued)

*Primary Examiner* — Paul Prebilic
(74) *Attorney, Agent, or Firm* — Brinks Gilson & Lione

(57) ABSTRACT

A stent graft has a cylindrical wall, an internal lumen within the cylindrical wall and a fenestration in the wall. The fenestration is closed off by a valve arrangement to prevent the flow of liquids from within the internal lumen to outside of the wall. The valve arrangement is a tube of graft material which can be closed off by pressure on its outside surface. The end of the tube remote from the fenestration can be held shut by having its periphery fastened to a flattened resilient ring. Fluid pressure on the tube of graft material causes the tube to close off to prevent fluid flow therethrough and by resilient deflection of the resilient ring the end of the tube of graft material can be opened to enable the passing of a medical device therethrough.

4 Claims, 5 Drawing Sheets

(51) Int. Cl.
    *A61F 2/86* (2013.01)
    *A61F 2/06* (2013.01)

(52) U.S. Cl.
    CPC ... *A61F 2002/061* (2013.01); *A61F 2002/075* (2013.01); *A61F 2230/0006* (2013.01); *A61F 2230/0008* (2013.01)

(58) Field of Classification Search
    CPC ........ A61F 2002/075; A61F 2230/0008; A61F 2230/0006; A61F 2250/0058; A61F 2250/006
    See application file for complete search history.

(56) References Cited

U.S. PATENT DOCUMENTS

| | | | |
|---|---|---|---|
| 5,713,917 A * | 2/1998 | Leonhardt | A61B 17/1219 606/194 |
| 5,733,337 A | 3/1998 | Carr, Jr. et al. | |
| 5,885,619 A | 3/1999 | Patel et al. | |
| 5,955,110 A | 9/1999 | Patel et al. | |
| 5,968,096 A | 10/1999 | Whitson et al. | |
| 6,494,909 B2 * | 12/2002 | Greenhalgh | A61F 2/2418 623/1.13 |
| 8,480,726 B2 * | 7/2013 | Cunningham | A61F 2/07 623/1.13 |
| 2002/0116047 A1 * | 8/2002 | Vardi | A61F 2/856 623/1.11 |
| 2003/0204243 A1 * | 10/2003 | Shiu | A61F 2/07 623/1.16 |
| 2005/0010277 A1 * | 1/2005 | Chuter | A61F 2/064 623/1.13 |
| 2005/0059923 A1 | 3/2005 | Gamboa | |
| 2007/0250154 A1 | 10/2007 | Greenberg et al. | |
| 2008/0147163 A1 * | 6/2008 | Allen | A61F 2/06 623/1.14 |
| 2009/0048663 A1 * | 2/2009 | Greenberg | A61F 2/07 623/1.35 |
| 2009/0210047 A1 | 8/2009 | Amplatz et al. | |
| 2011/0257725 A1 | 10/2011 | Argentine et al. | |
| 2012/0253471 A1 | 10/2012 | Tully et al. | |
| 2016/0302950 A1 * | 10/2016 | Marmur | A61F 2/07 |

FOREIGN PATENT DOCUMENTS

| | | | |
|---|---|---|---|
| EP | 14275165.0 | 3/2015 | |
| JP | 2003250907 | 9/2003 | |
| WO | 9822158 | 5/1998 | |
| WO | 2008057569 | 5/2008 | |
| WO | WO2011116307 A1 * | 9/2011 | ......... A61F 2/07 |
| WO | 2013115141 A1 | 8/2013 | |

OTHER PUBLICATIONS

Patent Examination Report No. 1 for corresponding AU Patent Application No. 2013254913 dated Feb. 27, 2014, 6 pages.
Patent Examination Report No. 2 for corresponding AU Patent Application No. 2013254913 dated Aug. 11, 2014, 4 pages.

* cited by examiner

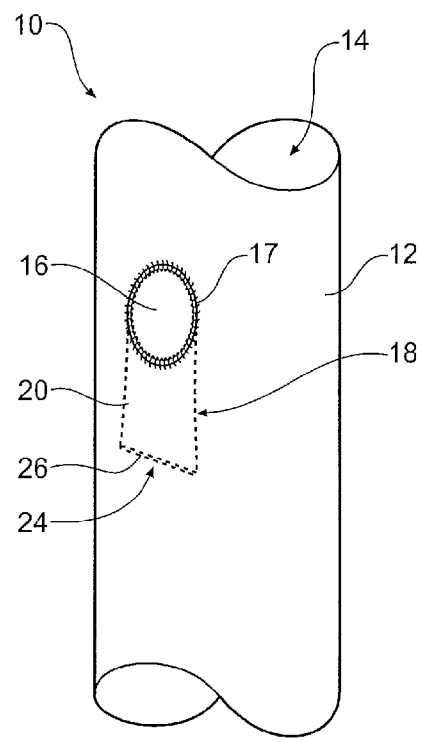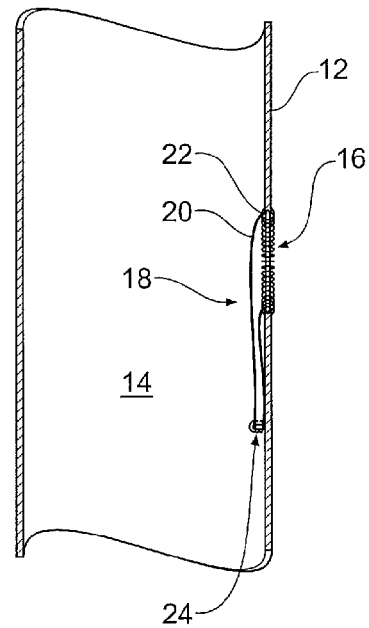
Fig 1        Fig 2
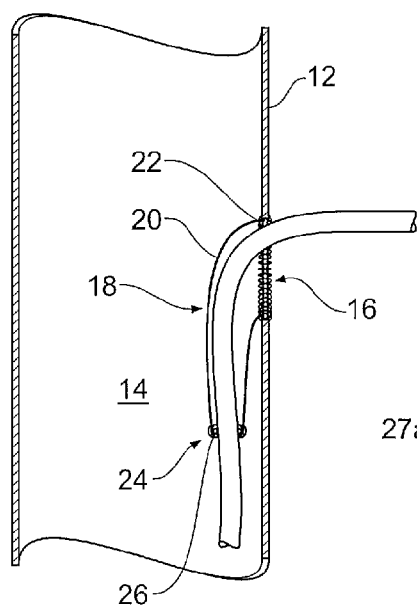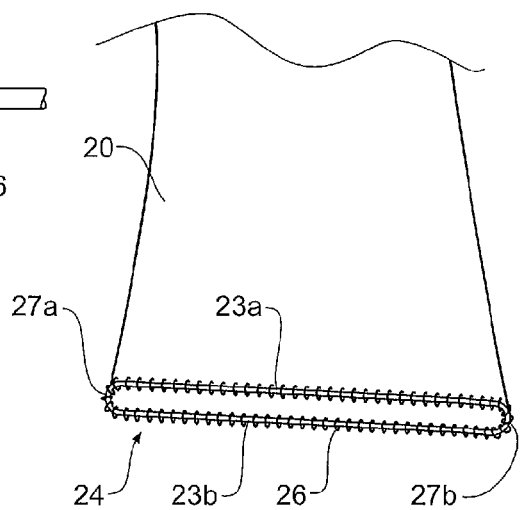
Fig 3        Fig 4

STENT GRAFT WITH VALVE ARRANGEMENT

FIELD OF INVENTION

This invention relates to a medical device and more particularly a device which can be deployed by endovascular means into the vasculature of a patient.

BACKGROUND OF THE INVENTION

There have been proposed endovascular devices which can be deployed into the vasculature, particularly in the region of the aortic bifurcation, so that an aneurysm in the aorta can be bridged by placement of the endovascular device with a proximal portion which seals into a non-aneurysed portion of the aorta adjacent to the renal arteries, a first leg which extends down one iliac artery to a non-aneurysed portion of the iliac artery and another short leg into which a leg extension may be placed to extend into a non-aneurysed portion of the contra-lateral iliac artery.

There can be problems, however, if the aneurysm of the aorta extends down into one or other of the iliac arteries. Each of the common iliac arteries branches into the internal and external iliac arteries and it is necessary in such a situation that a blood flow path can be directed through an endovascular stent graft into each of these arteries. In particular, it is desirable to introduce a leg extension onto the internal iliac artery from a bifurcation in the endovascular device. Access to the internal iliac artery for a medical device introducer through an already placed stent graft can be difficult from the contralateral iliac artery and hence there has been proposed, such as in US Patent Publication No. 20070250154, the use of a valve to facilitate access to the internal iliac artery. An introducer for the leg extension can be placed through the valve and after introduction of the leg extension the introducer can be withdrawn and the valve can then close to prevent blood loss from the endovascular device into the aneurysed region.

The object of this invention is to provide an endovascularly deployed medical device with a valve arrangement which can assist in solving this problem or at least provide a physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels, similar terms such as caudal and cranial should be understood.

DESCRIPTION OF THE INVENTION

In one form, the invention comprises a stent graft comprising a graft material defining a cylindrical wall, an internal lumen within the cylindrical wall and a fenestration in the wall, the fenestration comprising a valve arrangement to prevent the flow of liquids from within the internal lumen to outside of the wall;

the valve arrangement extending within the internal lumen and comprising a tube of graft material;

the tube of graft material comprising a first end and a second end, the first end being fastened to the wall around the fenestration and the tube extending into the internal lumen therefrom;

the second end comprising a pair of substantially parallel resilient struts and arcuate structures joining respective ends of the struts, the tube of graft material being fastened to resilient struts whereby the second end of the tube of graft material is substantially closed off at the second end;

whereby fluid pressure on an outside surface of the tube of graft material causes the tube to close off between the first end and the second end to prevent fluid flow therethrough and by resilient deflection of the resilient struts the second end of the tube of graft material can be opened to enable the passing of a medical device therethrough.

Preferably, the tube of graft material further comprises a resilient wire reinforcing structure comprising two longitudinal struts extending along the tube of graft material on diametrically opposed sides thereof, a ring structure at the first end of the tube of graft material and the longitudinal struts at the second end of the tube of graft material being fastened to the arcuate structures. The resilient wire reinforcing structure can comprise nitinol or stainless steel.

Each of the longitudinal struts can comprise a bend adjacent the first end thereof such that at rest the struts extend substantially parallel to the wall.

The tube of graft material comprises a biocompatible graft material which is heat set into the flattened cross section at the second end.

Alternatively, the tube of graft material can comprises a biocompatible graft material which is at least in part formed from a hybrid material able to be set into a flattened cross section at the second end. For instance, the hybrid material able to be set into the flattened cross section at the second end can comprise interwoven nitinol and Dacron.

In an alternative form, the invention comprises a stent graft comprising a tubular body of a biocompatible graft material defining a main lumen therethrough, an aperture in the tubular body and a valve arrangement to prevent fluid flow through the aperture from the inside of the tubular body to the outside of the tubular body, the valve arrangement comprises a valve assembly comprising a valve tube of biocompatible graft material and a support structure for the valve tube within the main lumen, the support structure comprising a pair of substantially parallel and spaced apart arms, a ring structure at one end of the spaced apart arms and a flattened ring structure at the other end of the spaced arms, the ring structure being fastened to the tubular body around the aperture and the valve tube comprising a first end and a second end, the first end of the valve tube being fastened around the ring structure at the one end of the spaced apart arms and the second end of the valve tube being fastened around the flattened ring structure at the other end of the spaced arms, at least the flattened ring structure at the other end of the spaced arms being formed of a resilient material such that the flattened ring structure can be opened by passing an object therethrough and returned to a closed state upon removal of the object.

Preferably, the pair of substantially parallel and spaced apart arms comprise a bend at the one end whereby the valve tube extends substantially along the tubular body.

In one embodiment, the tube of graft material comprises a cross sectional shape changing from substantially circular at the first end to be fastened around the fenestration to a flattened cross section at the second end to prevent fluid flow therethrough but by deflection of the flattened cross section the tube of graft material can be opened to enable the passing of a medical device therethrough.

Preferably, the tube of graft material comprises a biocompatible graft material which is heat set into the flattened cross section at the second end. Alternatively, the tube of graft material comprises a biocompatible graft material which is at least in part formed from a hybrid material able to be set into the flattened cross section at the second end. The hybrid material able to be set into the flattened cross section at the second end can comprise interwoven nitinol and Dacron.

In an alternative form, the invention comprises a valve arrangement in a wall of a stent graft, the wall defining an internal lumen of the stent graft;

a fenestration in the wall;

the valve arrangement extending within the internal lumen;

the valve arrangement comprising a tube of graft material;

the tube of graft material comprising a first end and a second end, the first end being fastened to the wall around the fenestration and the tube extending into the internal lumen;

whereby fluid pressure on the tube of graft material causes the tube to close off to prevent fluid flow therethrough.

In an alternative form, the invention comprises a valve arrangement in a wall of a stent graft, the wall defining an internal lumen of the stent graft;

a fenestration in the wall;

the valve arrangement comprising a tube of graft material supported at least in part by a resilient wire reinforcing structure;

the tube of graft material comprising a first end and a second end, the first end being fastened to the wall around the fenestration and the tube extending into the internal lumen;

the resilient wire reinforcing structure comprising two longitudinal struts extending along the tube of graft material on diametrically opposed sides thereof, a ring structure at the first end of the tube of graft material and a pair of substantially straight arms extending between the longitudinal struts at the second end of the tube of graft material, the tube of graft material being fastened to the pair of arms at the second end;

whereby the second end of the tube of graft material is closed off at the second end to prevent fluid flow therethrough but by resilient deflection of the pair of substantially straight arms, the tube of graft material can be opened to enable the passing of a device therethrough.

It will be seen by the various forms of the invention there is provided a valve arrangement and a stent graft with a valve arrangement through which a medical device can be deployed but upon removal of the medical device, the valve automatically closes to prevent fluid such as blood flowing through it.

While Dacron, expanded polytetrafluoroethylene (ePTFE), or other synthetic biocompatible materials can be used for the tubular graft material for the stent graft and the valve tube, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogenic biomaterials, such as SIS, autologous tissue can be harvested as well, for use in forming the tubular graft material. Additionally, Elastin or Elastin-Like Polypeptides (ELPs) and the like offer potential as a material to fabricate the tubular graft material to form a device with exceptional biocompatibility.

SIS is available from Cook Biotech, West Lafayette, Ind., USA.

It will be seen that by this invention there is provided a stent graft with a valve arrangement. The valve arrangement allows an indwelling catheter to be provided through the valve into a side arm in the iliac artery at the time of deployment to assist with deployment of a leg extension into the internal iliac artery.

This then generally describes the invention but to assist with understanding, reference will now be made to the accompanying drawings which show embodiments of the invention.

BRIEF DESCRIPTION OF THE DRAWINGS

In the drawings;

FIG. 1 shows a first embodiment of stent graft according to the present invention;

FIG. 2 shows a longitudinal cross section of the embodiment shown in FIG. 1;

FIG. 3 shows the longitudinal cross section shown in FIG. 2 but with a sheath of a medical device extending through the valve arrangement;

FIG. 4 shows a detailed view of the second end of the tube of the embodiment shown in FIG. 1;

DESCRIPTION OF PREFERRED EMBODIMENTS

Figure 5:
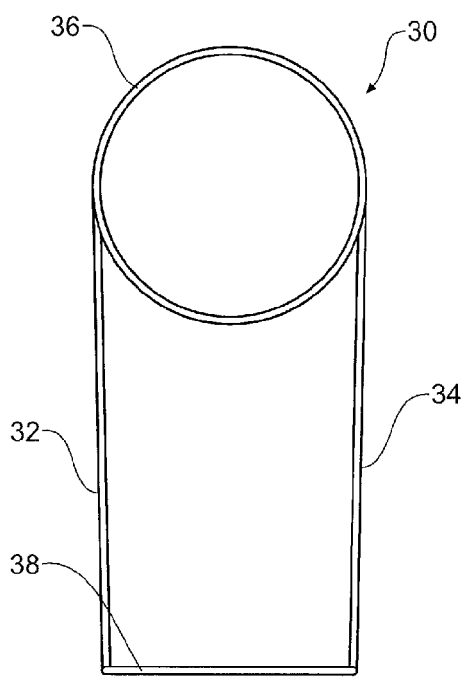
FIG. 5 shows a front view of wire reinforcement suitable for a valve arrangement of an alternate embodiment of valve arrangement.
Figure 6:
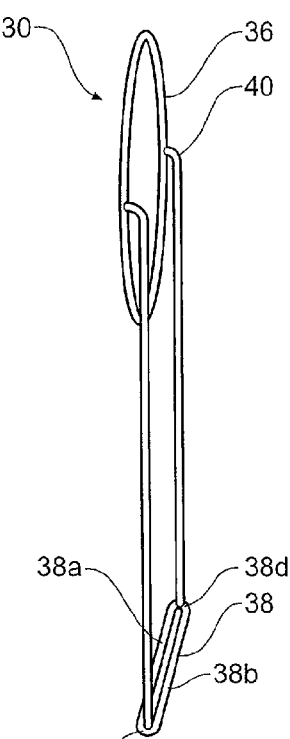
FIG. 6 shows a side view of the wire reinforcement shown in FIG. 5.
Figure 7:
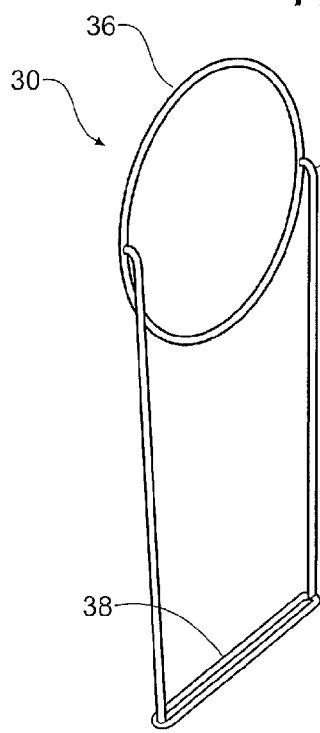
FIG. 7 shows a perspective view of the wire reinforcement shown in FIG. 5.
Figure 8:
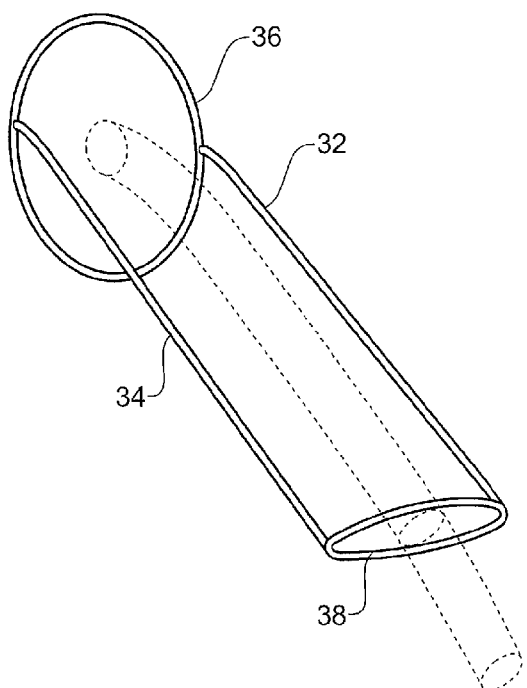
FIG. 8 shows the perspective view as in FIG. 7 but with a sheath of a medical device shown schematically extending therethrough.

FIGS. 1 to 4 show a first embodiment of a stent graft and valve according to the present invention. FIG. 1 shows an outside view, FIG. 2 shows a longitudinal cross section of the embodiment shown in FIG. 1, FIG. 3 shows the longitudinal cross section shown in FIG. 2 but with a sheath of a medical device extending through the valve arrangement and FIG. 4 shows a detailed view of the second end of the tube of the embodiment shown in FIG. 1.

The stent graft 10 comprises a tubular wall 12 of a biocompatible graft material. The tubular wall may be supported by self-expanding or balloon expandable stents (not shown). The tubular wall defines an internal lumen 14. There is a fenestration 16 in the wall 12. The fenestration can be bounded by a circular ring structure 17 stitched into the tubular wall 12. A valve assembly 18 is fastened to the wall 12 around the fenestration and the valve assembly 18 extends within the internal lumen 14. The valve assembly 18 is constructed to prevent fluid flow, such as blood flow, from passing through the fenestration from the internal lumen 14 to the outside of the stent graft.

The valve assembly 18 comprises a tube of graft material 20. The tube of graft material has a first end 22 and a second end 24, the first end 22 fastened to the wall 12 around the fenestration 16 and the tube extends into the internal lumen 14 from the fenestration 16. Fluid pressure, such as blood pressure on the outside surface of the tube of graft material, causes the tube to flatten out and lie against the inside of the wall 12 and therefore close off to prevent fluid flow through the tube.

The valve assembly has a resilient wire reinforcing structure at the second end 24. The resilient wire reinforcing structure is formed from a pair of substantially parallel resilient struts 23a and 23b and arcuate structures 27a and 27b joining respective ends of the struts to form what is essentially flattened ring structure 26 at the second end 24 of the tube 20. The flattened ring structure 26 can be formed from nitinol wire or stainless steel wire.

The tube of graft material is fastened by stitching 25, for instance, around the flattened ring structure 26, and by this means the second end of the tube of graft material is substantially closed off at the second end. This allows the two sides of the graft material to be close together and touch together to prevent fluid flow therethrough when the resilient ring is in its rest state. By resilient deflection of the flattened ring structure 26, such as by passing a dilator and sheath therethrough, the flattened ring structure 26 and the tube 20 of graft material can be opened to enable the passing of a medical device therethrough. Upon removal of the medical device, the flattened ring structure can retain its rest shape, which will allow the two sides of the graft material to be close together and touch together to prevent fluid flow therethrough.

Additionally, the tube of graft material can comprise a resilient wire reinforcing structure, such as that shown in FIGS. 5 to 8. For clarity, the resilient wire reinforcing structure shown in FIGS. 5 to 8 does not show the tube of graft material. The resilient wire reinforcing structure 30 comprises two longitudinal struts 32, 34 extending along where the tube of graft material would be and on diametrically opposed sides thereof, a ring structure 36 at the first end of two longitudinal struts 32, 34 and a pair of arms 38 extending between the longitudinal struts 32, 34 at the second end of the tube of graft material. The pair of arms 38 extending between the longitudinal struts 32, 34 at the second end of the tube of graft material essentially form a flattened ring in the same manner as discussed in relation to FIGS. 1 to 4.

As with the earlier embodiment, the flattened ring structure can be described as being formed from a pair of substantially parallel resilient struts 38a and 38b and arcuate structures 38c and 38d joining respective ends of the struts 38a and 38b.

The second end of tube of graft material is fastened around its circumference to the flattened ring. By this arrangement, the second end of the tube of graft material is substantially closed off at the second end, which assists in flattening the tube to prevent fluid flow therethrough when there is fluid pressure on the outside of the tube. By resilient deflection of the pair of arms, such as by passing a dilator and sheath therethrough, the pair of arms and the tube of graft material can be opened to enable the passing of a medical device therethrough. The resilient wire reinforcing structure can be formed from nitinol or stainless steel.

The ring a ring structure 36 at the first end of two longitudinal struts 32, 34 is fastened into the tubular wall 12 in use and provided support for the fenestration.

To assist with the tube of graft material lying against the inside wall of the stent graft at rest, and thereby providing minimum obstruction to the flow of liquid such as blood through the stent graft, the two longitudinal struts 32, 34 extending along the tube of graft material can have a bend 40 at their upper ends adjacent to the ring 36. When a dilator and sheath is passed through the tube of graft material, the bends 40 can be straightened out against the resiliency of the struts and the dilator and sheath can be directed in any desired direction.

Figure 9:
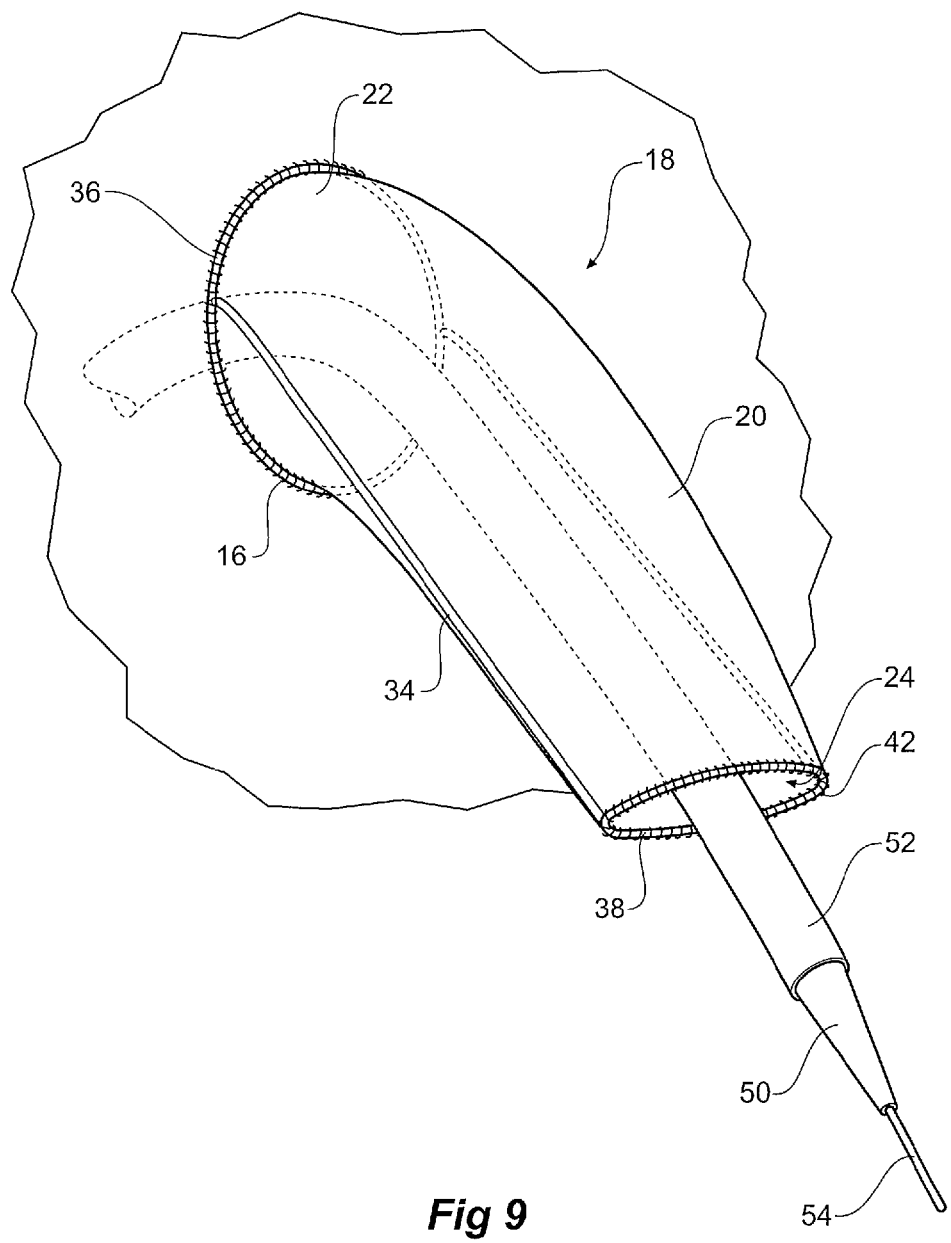
FIG. 9 shows a perspective view of a valve arrangement incorporating the wire reinforcement of FIGS. 5 to 8 and with a sheath of a medical device shown schematically extending therethrough.

FIG. 9 shows a part of a stent graft with a valve arrangement according to the present invention with a dilator and sheath passed therethrough.

The wall of the stent graft 12 has a fenestration with the valve arrangement 18 mounted into a fenestration 16 in the wall. The valve assembly 18 comprises a tube of graft material 20. The tube of graft material has a first end 22 and a second end 24, the first end 22 fastened to the wall 13 around the fenestration 16 and the tube extends into the internal lumen of the stent graft from the fenestration 16. The valve arrangement has a resilient reinforcement structure 30. The resilient wire reinforcing structure 30 comprises two longitudinal struts 32, 34 extending along the tube of graft material 20 on diametrically opposed sides thereof, a ring structure 36 at the first end of the tube of graft material is stitched around the fenestration 16 and holds open the fenestration. A pair of arms 38 extend between the longitudinal struts 32, 34 at the second end 24 of the tube of graft material 20. The second end 24 of tube of graft material is fastened around its circumference to the pair of arms by stitching 42.

In this illustration, a dilator 50 and sheath 52 have been deployed over a guide wire 54, which passes through the valve arrangement 18 and these have opened up the pair of arms 38 against the resiliency of the arms. When the dilator 50 and sheath 52 are removed, the arms close up the second end of the valve arrangement so that the sides of the tube engage each other due to liquid pressure outside the tube and close off the valve arrangement.

Figure 10:
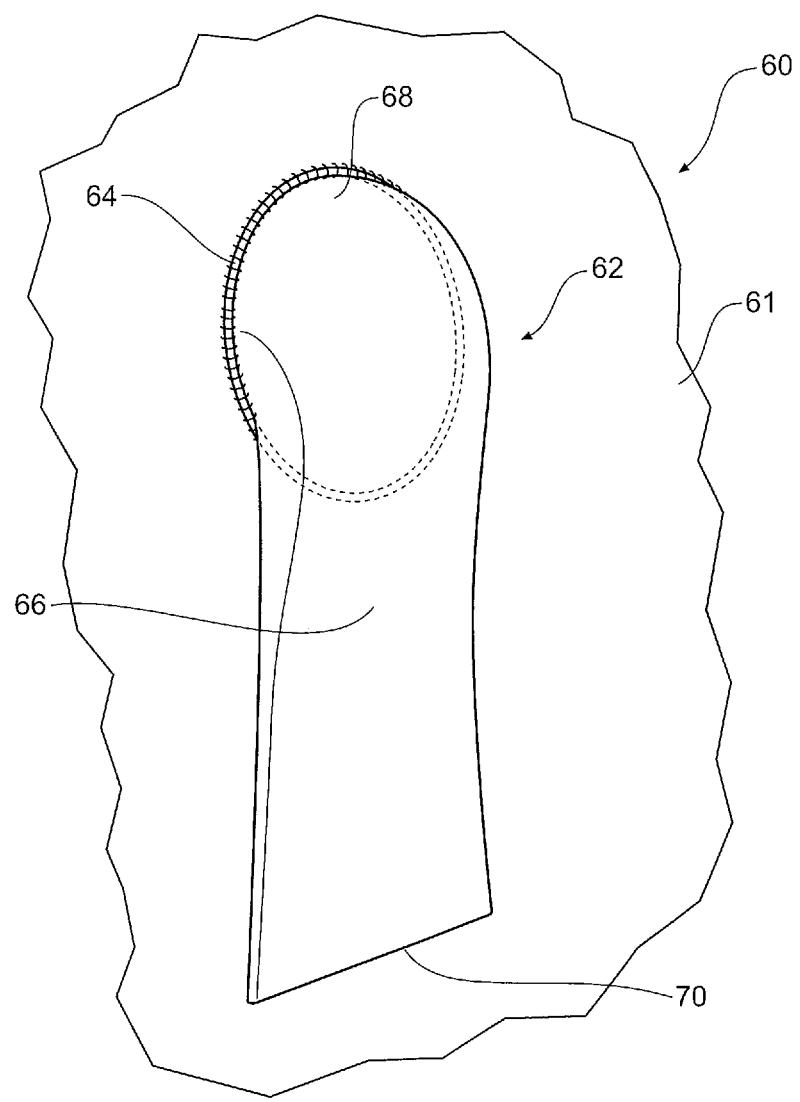
FIG. 10 shows a perspective view of an alternative embodiment of a valve according to the present invention.
Figure 11:
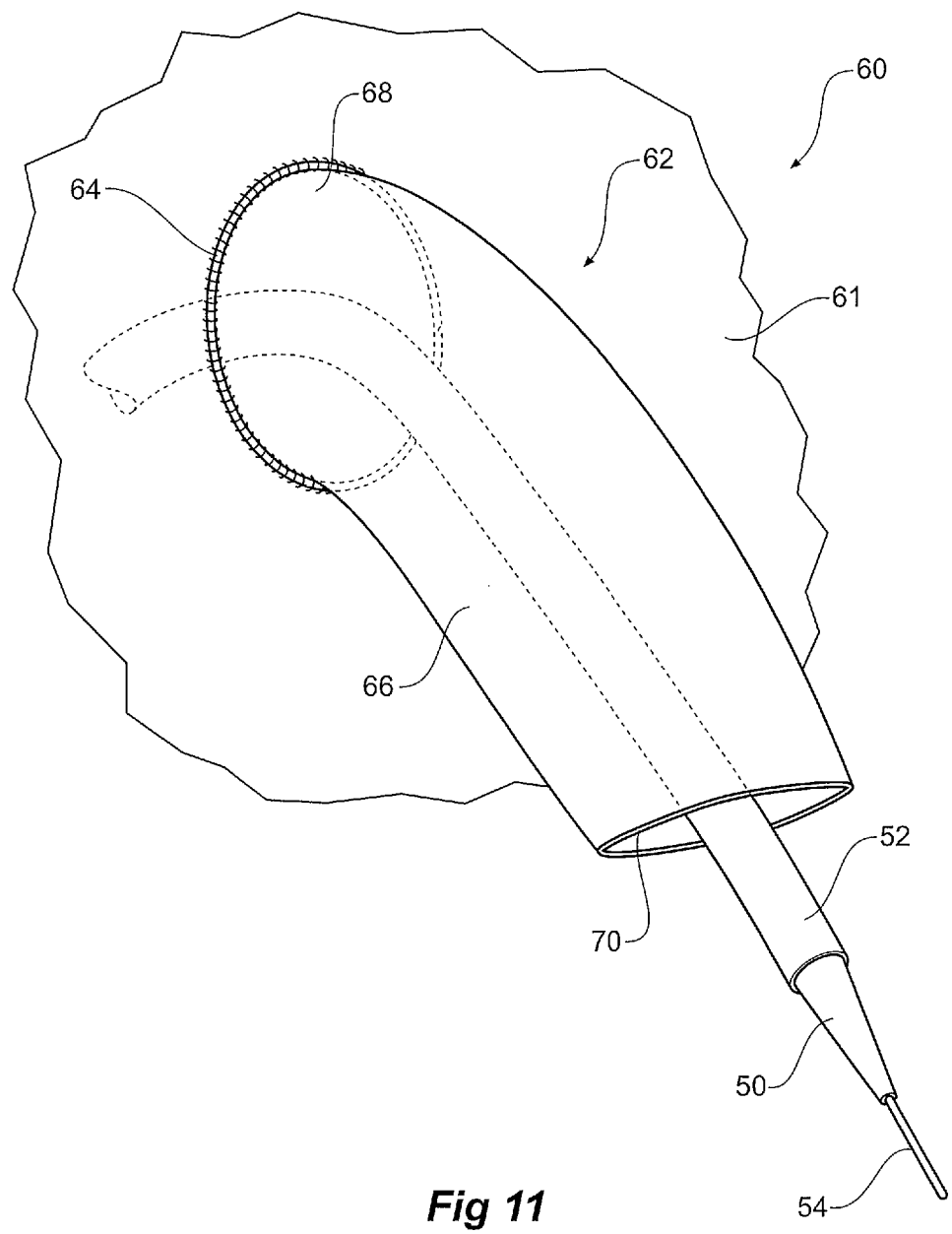
FIG. 11 shows a perspective view of the valve arrangement of FIG. 10 with a sheath of a medical device shown schematically extending therethrough.

FIG. 10 shows a perspective view of an alternative embodiment of a valve arrangement according to the present invention and FIG. 11 shows a perspective view of the valve arrangement of FIG. 9 with a sheath of a medical device shown schematically extending therethrough.

In this embodiment, the inside wall 61 of the stent graft 60 has a fenestration with the valve arrangement 62 mounted into a fenestration 64 in the wall. The valve assembly 62 comprises a tube of graft material 66. The tube of graft material has a first end 68 and a second end 70, the first end 68 fastened to the wall 61 around the fenestration 64 and the tube extending into the internal lumen of the stent graft from the fenestration 64. The tube of graft material 66 of the valve arrangement 62 is formed from a flexible biocompatible graft material such as Dacron. The tube of graft material 66 comprises a cross sectional shape changing from substantially circular at the first end 68 to be fastened around the fenestration 64 to a flattened cross section at the second end 70.

The flexible nature of the tube of graft material 66 allows it to hang down substantially parallel to the wall 61 of the stent graft 60. Fluid flow and pressure, such as by blood flow through the stent graft in use, on the outer surface of the tube of graft material causes the tube to hang down and be pressed against the wall of the stent graft and to thereby close off to prevent fluid flow through the tube of graft material 66. By deflection of the flattened cross section, the tube of graft material can be opened to a more tubular shape to enable the passing of a medical device therethrough.

In one embodiment, the tube of graft material comprises a biocompatible graft material which is heat set into the flattened cross section at the second end.

Alternatively, the tube of graft material comprises a biocompatible graft material which is at least in part formed from a hybrid material able to be set into the flattened cross section at the second end. Such a hybrid material which is able to be set into the flattened cross section at the second end can be interwoven nitinol and Dacron.

In FIG. 11, a dilator 50 and sheath 52 have been deployed over a guide wire 54 which passes through the valve arrangement 62 and these have opened up the flattened second end 70. When the dilator 50 and sheath 52 are removed, the flattened end 70 closes up again so that the sides of the tube engage each other due to liquid pressure outside the tube and close off the valve arrangement.

In another embodiment the invention includes a valve arrangement 18 in a wall 12 of a stent graft 10, the wall defining an internal lumen 14 of the stent graft; a fenestration 16 in the wall; the valve arrangement extending within the internal lumen; the valve arrangement comprising a tube of graft material 20; the tube of graft material comprising a first end 22 and a second end 24, the first end being fastened to the wall around the fenestration and the tube extending into the internal lumen; whereby fluid pressure on the tube of graft material causes the tube to close off to prevent fluid flow therethrough; the tube of graft material 20 comprising a cross sectional shape changing from substantially circular at the first end 22 to be fastened around the fenestration to a flattened cross section at the second end 24 to prevent fluid flow therethrough but by deflection of the flattened cross section the tube of graft material can be opened to enable the passing of a medical device therethrough.

In the embodiment above, the tube of graft material 20 may also comprise a biocompatible graft material which is heat set into the flattened cross section at the second end or the tube of graft material may comprise a biocompatible graft material which is at least in part formed from a hybrid material able to be set into the flattened cross section at the second end. The hybrid material able to be set into the flattened cross section at the second end 24 may comprise interwoven nitinol and Dacron.

What is claimed is:
1. A stent graft comprising,
a first end;
a second end;
a sidewall of graft material between the first end and the second end, the wall defining an internal lumen of the stent graft;
a fenestration extending through the sidewall from an exterior of the stent graft to the interior of the stent graft;
a valve arrangement extending within the internal lumen;
the valve arrangement comprising a tube of graft material;
the tube of graft material comprising a first end and a second end, the first end being fastened to an inside surface of the sidewall around the fenestration and the tube extending from the fenestration into the internal lumen;
wherein the second end of the tube of graft material is biased into a flattened and closed configuration and a remainder of the tube from the fenestration to the second end is in an open and tubular configuration and configured to be flattened against the inside surface of the side wall upon application of fluid pressure to the tube to prevent fluid flow therethrough, such that the cross section of the entire remainder of the tube of graft changes from a substantially circular cross section to a flattened cross section at the second end upon the application of the fluid pressure but by deflection of the flattened cross section the tube of graft material can be opened to enable the passing of a medical device therethrough.

2. A stent graft as in claim 1, wherein the tube of graft material further comprises a biocompatible graft material which is heat set into the flattened cross section at the second end.

3. A stent graft as in claim 1, wherein the tube of graft material comprises a biocompatible graft material which is at least in part formed from a hybrid material able to be set into the flattened cross section at the second end.

4. A stent graft as in claim 3, wherein the hybrid material able to be set into the flattened cross section at the second end comprises interwoven nitinol and polyethylene terephthalate.

\* \* \* \* \*